United States Patent [19]
Trull

[11] Patent Number: 5,947,929
[45] Date of Patent: Sep. 7, 1999

[54] FRONT-LOAD ANGIOGRAPHIC INJECTOR SYSTEM, ANGIOGRAPHIC SYRINGE AND PLUNGER FOR ANGIOGRAPHIC SYRINGE

[75] Inventor: Michael Wayne Trull, Apex, N.C.

[73] Assignee: Coeur Laboratories, Inc., Raleigh, N.C.

[21] Appl. No.: 08/916,369

[22] Filed: Aug. 22, 1997

[51] Int. Cl.⁶ ...................................................... A61M 1/00
[52] U.S. Cl. ...................... 604/152; 604/187; 604/131; 604/151
[58] Field of Search ...................................... 604/154, 187, 604/181, 218, 219, 228, 152, 131; 128/DIG. 1

[56] References Cited

U.S. PATENT DOCUMENTS

| | | |
|---|---|---|
| 3,156,236 | 11/1964 | Williamson . |
| 3,631,847 | 1/1972 | Hobbs, II . |
| 3,880,138 | 4/1975 | Wootten et al. . |
| 4,006,736 | 2/1977 | Kranys et al. . |
| 4,582,218 | 4/1986 | Ross . |
| 4,677,980 | 7/1987 | Reilly et al. . |
| 4,846,796 | 7/1989 | Carrell et al. . |
| 4,846,797 | 7/1989 | Howson et al. . |
| 4,869,720 | 9/1989 | Chernack . |
| 4,911,695 | 3/1990 | Lindner . |
| 5,006,112 | 4/1991 | Metzner . |
| 5,007,904 | 4/1991 | Densmore et al. . |
| 5,155,960 | 10/1992 | Shannan . |
| 5,176,646 | 1/1993 | Kuroda . |
| 5,279,583 | 1/1994 | Shober, Jr. et al. . |
| 5,300,031 | 4/1994 | Neer et al. . |
| 5,383,858 | 1/1995 | Reilly et al. ............................ 604/152 |
| 5,535,746 | 7/1996 | Hoover et al. ...................... 604/152 X |

*Primary Examiner*—Wynn Wood Coggins
*Assistant Examiner*—N. Kent Gring
*Attorney, Agent, or Firm*—William A. Barrett; Steven J. Hultquist

[57] ABSTRACT

An angiographic syringe and plunger therefor, having utility in a power-driven angiographic syringe injector apparatus comprising an axially extending drive shaft and a frustoconical-shaped driving head attached to the shaft. The plunger is constructed to engage the driving head, with a circumferentially extended array of circumferentially spaced-apart flexible resilient engagement members which compressively bear on the side and rear surfaces of the frustoconical driving head. The flexible resilient engagement members are radially inwardly offset from the edge of the plunger, to avoid contact with inner surfaces of the syringe barrel contamination of the interior volume of the syringe. The syringe is mounted on the injector apparatus by a face plate adapter assembly serving to position the flexible resilient engagement members for coupling to the driving head. Plunger and driving head elements are described which are interactive with a face plate adapter assembly to engage and disengage the plunger and driving head in relation to one another.

48 Claims, 9 Drawing Sheets

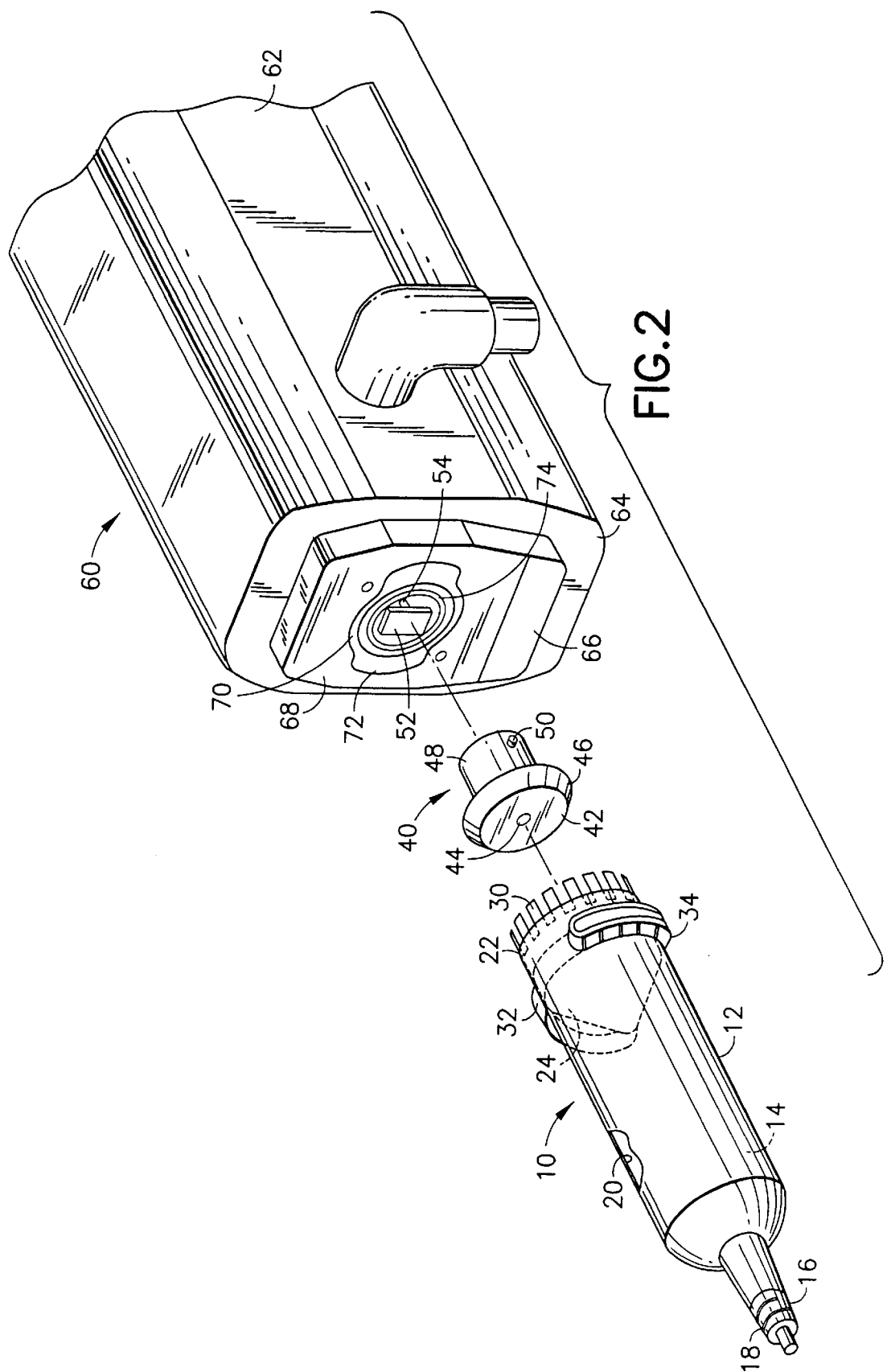

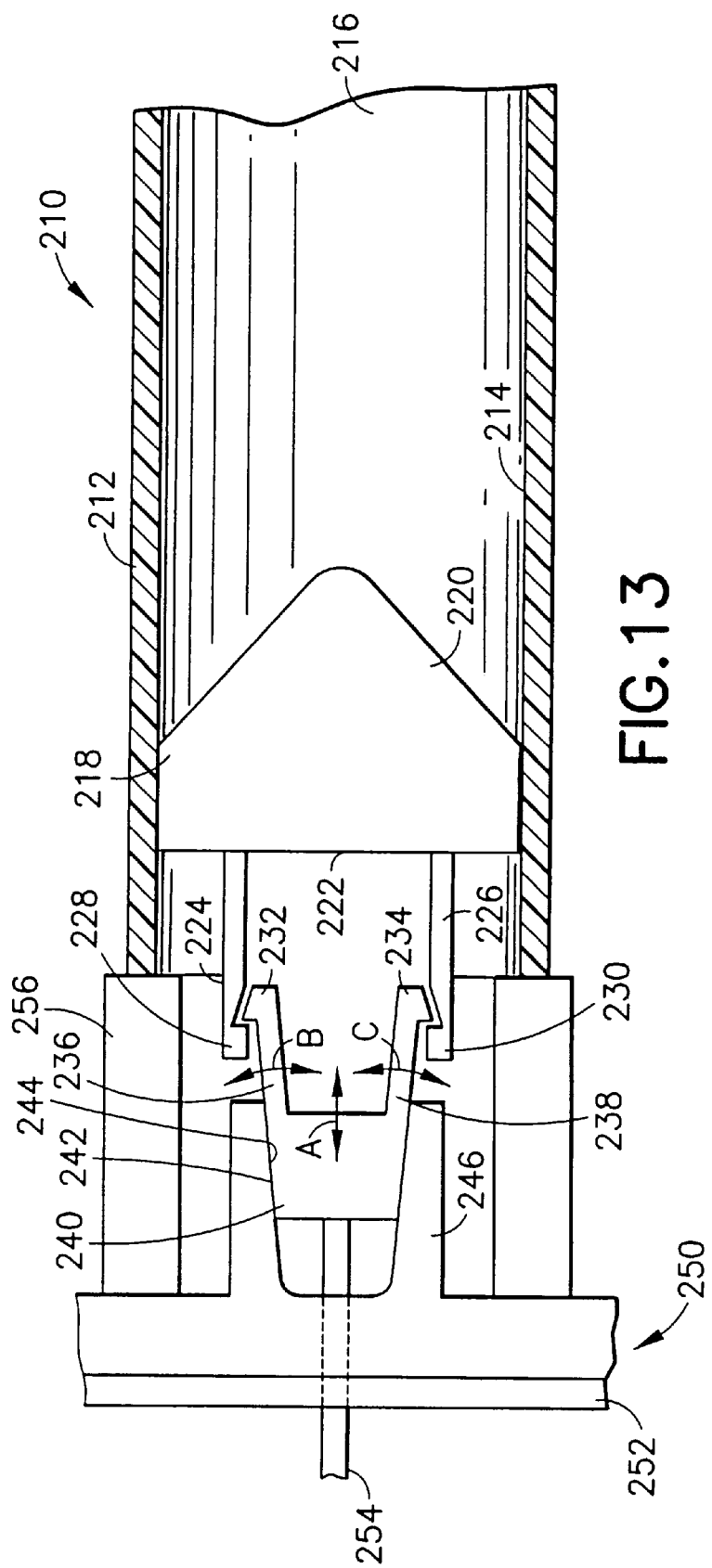

FRONT-LOAD ANGIOGRAPHIC INJECTOR SYSTEM, ANGIOGRAPHIC SYRINGE AND PLUNGER FOR ANGIOGRAPHIC SYRINGE

BACKGROUND OF THE INVENTION

1. Field of the Invention

This invention generally relates to power-driven angiographic syringes, and specifically to a plunger for such a syringe, and to a syringe and power injector system comprising same.

2. Description of the Related Art

In the field of angiography, a contrast medium of suitable indicating character (radiopacity) is introduced under pressure into coronary arteries, and the arterial network then is monitored by fluoroscopic or other visualizing means. As a result, arterial plaque deposits and/or other arterial occlusions are readily visually determined as to their size and location, so that suitable treatment methods, such as removal of the occluding material by lasing or mechanical excision, or by displacement techniques such as balloon angioplasty, may be carried out.

To effect the introduction of the contrast medium into the arterial network for angiographic study, it has been common practice to utilize injector syringes in combination with arterial catheters. The syringe may be machine-mounted in a so-called "power injector" apparatus, with the distal end of the syringe being connected to the catheter which is introduced into the arterial system to be studied.

There is disclosed in U.S. Pat. No. 4,677,980 issued Jul. 7, 1987 to D. M. Reilly, et al., an angiographic power injector featuring a rotating turret for housing multiple angiography syringes in readiness for injection. In use, the turret is selectively rotated to align an angiographic syringe with a driving mechanism of the power injector. Specifically, as is shown in FIGS. 9 and 10 of this patent, the plunger of the angiographic syringe may be configured with rearwardly extending hook members which are engaged by the head and stem portion (typically termed a "ram" in the field) of the driving mechanism.

In the plunger configuration disclosed in this patent, the hook elements on the proximal face of the plunger are diametrally opposed to one another, to form a slot therebetween through which the ram head is inserted and subsequently rotated. The head is of transversely extending character, so that it thereby engages the respective hook members. In this manner, the head and stem of the driving mechanism and the hook members are described to constitute a quick release driving connection, with the driving mechanism head fitting into the aperture formed by the hook members, and with the stem extending out from the aperture through the access slot between the hook members.

The Reilly et al. patent, at column 6, lines 24–52 thereof, describes the subsequent operation of the coupled syringe. First, the driving mechanism is forwardly translated to drive the plunger through the syringe to expel air therefrom. Next, the syringe is connected to a source of contrast media and the driving mechanism is retracted to pull the plunger back through the syringe, to draw contrast media thereinto. Finally, the driving mechanism is advanced to drive the plunger distally in the syringe and effect injection of the contrast media through a catheter attached to the syringe. The patent states that after the injection has been carried out, the driving mechanism may be disengaged from the plunger, without reversing its movement, by the simple expedient of rotating the driving mechanism 90°, so that the driving mechanism head extends from the aperture on either side (see FIG. 10 of the patent). Subsequent retraction of the driving mechanism results in the head and stem of the driving mechanism being withdrawn from the aperture and slot, thereby disengaging the driving mechanism from the plunger.

As a result of the foregoing configuration of the driving mechanism, and the hook members on the plunger, the risks incident to retracting the plunger through the syringe during the angioplasty procedure are said to be eliminated, and the mating hook members and driving mechanism head are said to cooperate so that the plunger can be placed in either a driven retractable state, or an undriven non-retractable state, at any time during the injection operation and at any position of the plunger, without substantial force being applied therebetween.

While the foregoing configuration of the hook members on the plunger facilitates the engagement and disengagement of the driving mechanism, without change in the position of the plunger, it also is true that the hook members themselves provide only a very small contact area for mating with the head of the driving mechanism, when the driving mechanism is in driving or retraction engagement with the hook members.

There is thus the danger that the head of the driving mechanism may disengage from contact with the hook members during operation of the syringe, so that subsequent rotation of the driving mechanism to effect disengagement actually effects re-engagement of the driving mechanism with the hook members, in turn causing retraction of the plunger, an occurrence which is specifically desired to be avoided.

The Reilly et al. patent discloses other plunger and driving mechanism constructions, e.g., as shown in FIGS. 11–21 of the patent, but all such alternative constructions are relatively more complex in construction and operation.

U.S. Pat. No. 5,007,904 issued Apr. 16, 1991 in the names of L. L. Densmore and T. A. Lindner, discloses an angiographic syringe plunger having a generally converging distal portion, and a rear face of which is provided a coupling structure which is transversely engageable by, and transversely disengageable from, a driving mechanism of a power-driven angiographic syringe. Once engaged by the driving mechanism, the plunger cannot be disengaged solely by rotation of the driving mechanism relative to the plunger in the absence of transverse translational movement of the driving mechanism and plunger relative to one another. The coupling structure disclosed in this patent includes a wall extending rearwardly from the proximal face of the plunger body and partially circumferentially thereon. The wall terminates at a proximal extremity, and a radially inwardly extending flange is joined at an outer peripheral portion thereof to the proximal extremity of the wall. In such manner, the radially inwardly extending flange and the wall form with the proximal face of the plunger a cavity transversely open to insertion of a ram head thereinto. For example, the coupling structure described in this patent may be generally C-shaped, with a continuously curved portion having an arc length not exceeding about 180°, and optionally provided with tangentially extending end segments respectively joined to the extremities of the continuously curved portion.

U.S. Pat. No. 4,199,695 issued Mar. 27, 1990 to Thomas A. Lindner discloses another plunger for a power-driven angiographic syringe assembly. The plunger includes a plunger body having a generally convergent distal portion and a proximal face. Laterally spaced-apart retention members are disposed on the proximal face in diametrally opposite relationship to one another, for retaining the power driving means in position once engaged with the plunger. Each of the retention members comprises a leg portion extending generally rearwardly from the proximal face and joined at a rearward part to a bridge segment laterally inwardly extending therefrom toward the other retention member, to an inner extremity, which is in spaced relationship to the corresponding inner extremity of the bridge segment of the other retention member. The inner extremities of the bridge segments thereby define a spacing accommodating transverse passage of the drive shaft therethrough. The leg portions and bridge segments of the retention members together define with the proximal face of the plunger a lateral slot accommodating transverse passage of the driving head therethrough. Transversely outwardly extending flexible, resilient flange elements are joined to the inner extremity of each of the aforementioned bridge segments and form laterally spaced-apart, transversely aligned pairs of flange elements on either side of the bridge segments, defining a transverse channel therebetween. The flange elements are shaped to define marginal portions of the transverse channel having a reduced channel width relative to a medial portion thereof. The marginal channel portions allow transverse passage of the drive shaft therethrough by deforming the flange elements bounding the marginal channel portions, so that the drive shaft thereafter is retentively held in the medial portion of the transverse channel, to accommodate free rotation of the driving mechanism relative to the plunger, without disengaging the driving mechanism from the plunger.

U.S. Pat. No. 5,383,858 issued Jan. 24, 1995 to David M. Reilly, et al. describes a front-loading injector and syringe assembly, in which the syringe is mountable on and removable from a front wall of the injector housing. The front wall of the housing has a face plate presenting a pair of slots for receiving retaining flanges on the proximal end of the syringe. The syringe thus is inserted with the proximal end flanges passing through the slots, and then the syringe is rotated to engage the flanges behind associated retaining flanges of the face plate. The syringe contains a plunger with a proximal face having hook-like elements which engage with the ram tip of the injector apparatus. The ram tip is of elongate character and passes into the slot between the hook-like members on the proximal face of the plunger, so that subsequent rotation of the syringe into locking position engages the hook-like members with the end portions of the ram tip.

It is an object of the present invention to provide an improved front-loading syringe and injector apparatus comprising same, for injection of liquid contrast media or other fluid.

It is another object of the present invention to provide a plunger which is readily engageable with the driving mechanism of a front-load power injector system, without the necessity for registration and rotational locking.

It is a further object of the present invention to provide a face plate structure accommodating such a plunger and associated angiographic syringe.

It is yet another object of the present invention to provide a plunger structure which avoids any contamination of the internal surfaces of the syringe during loading of the syringe with contrast fluid or other media to be dispensed therefrom.

Other objects and advantages of the present invention will become more fully apparent from the ensuing disclosure and appended claims.

SUMMARY OF THE INVENTION

In a broad aspect, the present invention relates to a front-load syringe injector system including a front-load injector apparatus having mounted on a front face thereof a face plate adapter assembly, with a driving head engaged with a drive mechanism of the injector and such driving head disengageably engaging a plunger mounted in an angiographic syringe mounted on a front face of the front-load syringe injector, wherein at least one of the plunger and driving head elements interacts with the face plate to effect engagement and disengagement of the plunger and driving head with respect to one another.

In one specific aspect, the present invention relates to a plunger for an angiographic syringe having utility in a power-driven angiographic front-loading syringe assembly comprising power driving means including an axially extending reciprocatable driving shaft and a frustoconical shaped driving head attached to the drive shaft.

The plunger includes a plunger body having a generally convergent distal portion and a proximal face.

The plunger body has an outer circumferentially continuous edge surface for engaging an interior surface of a syringe barrel when the plunger is operatively positioned within the syringe barrel.

The proximal face of the plunger includes a circumferential surface portion. An array of circumferentially spaced-apart flexible resilient engagement members is joined to the circumferential surface portion of the proximal face of the plunger body and rearwardly extends therefrom. Each of the flexible resilient engagement members has a shank portion rearwardly extending from the circumferential surface portion and terminating in a tail hook portion including a transversely and radially inwardly extending retention surface for matably engaging with a rear circumferential surface of a drive head of an injector when the drive head is operatively coupled with the plunger. Each tail hook portion at the retention surface is of increased thickness relative to the shank portion of the flexible resilient engagement member and of tapering character toward a rearmost extremity thereof, with a convexly shaped inner engagement surface for contacting the frustoconical shaped drive head to circumferentially compressively engage a frustoconical side surface of the driving head with the transversely and radially inwardly extending retention surface matably engaged with a rear circumferential surface of the driving head when the driving head is engaged with the plunger. The array of circumferentially spaced-apart flexible resilient engagement members is circumferentially arranged on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the barrel.

A further aspect of the invention relates to an angiographic syringe including a plunger of the above-described type.

Another aspect of the invention relates to a face plate adapter assembly for a front-load syringe injector, including a main body having on a rear face thereof a cylindrical extension with diametrally opposite flange elements for engaging a matably shaped cavity on a front face of an injector apparatus, and lockable in position by rotation thereof so that the diametrally opposite flange elements engage retaining flange elements in the face of the injector apparatus, with a front face having a cylindrical cavity therein and a front slot opening communicating therewith with diametrally opposite retention flange portions transverse to the slot opening, for engagement with a front-load syringe having rear flange members engageable with the slot opening and lockable in position in the face plate adapter assembly by rotation so that the rear flange members of the syringe engage the retention flange portions of the main body.

The face plate main body has in the cavity a lifting ring defining an annular volume between the cavity and the lifting ring for engagement with a rear circumferential extremity of a syringe when the syringe is engaged with the face plate adapter assembly. The lifting ring serves to engage with and radially outwardly spread the flexible resilient engagement members of the plunger in the aforementioned syringe assembly comprising the plunger of the invention.

In a further aspect, the invention relates to a front-load injector system comprising an angiographic syringe including a plunger of the above-described construction.

Other aspects and features of the invention will be more fully apparent from the ensuing disclosure and appended claims.

BRIEF DESCRIPTION OF THE DRAWINGS

FIG. 2 is a perspective view of an angiographic syringe of a general type as shown in FIG. 1, in exploded view relationship to a face plate adapter assembly of a front-load syringe injector assembly, according to another aspect of the invention.

FIG. 13 is a cross-sectional elevation view of a portion of an angiographic syringe and plunge according to another embodiment of the present invention, with a face plate adapter assembly of alternative design.

DETAILED DESCRIPTION OF THE INVENTION, AND PREFERRED EMBODIMENTS THEREOF

Figure 1:
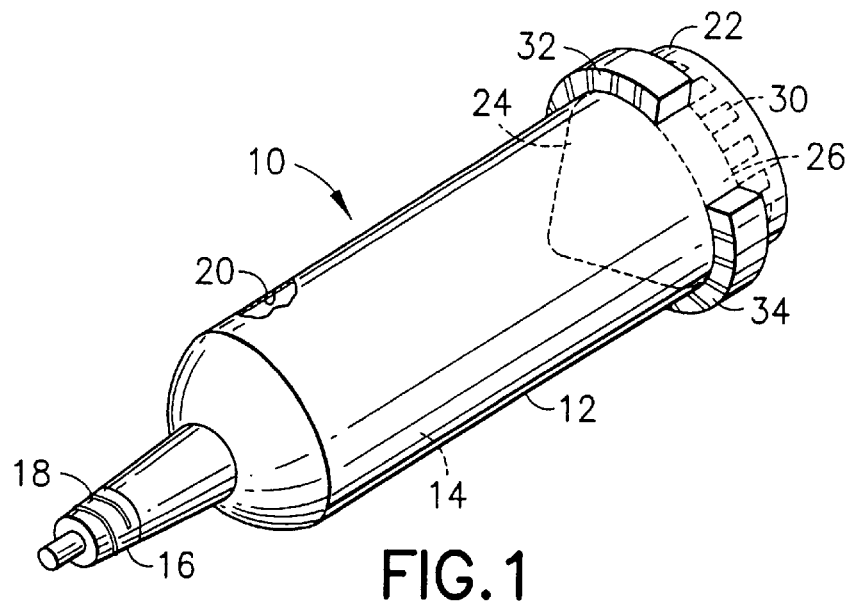
FIG. 1 is a perspective view of an angiographic syringe according to one embodiment of the present invention.

FIG. 1 is a perspective view of an angiographic syringe 10 according to one embodiment of the present invention. As shown, the syringe includes a main cylindrical barrel 12 enclosing an inner volume 14 which in use of the syringe is filled with contrast media or other solution or liquid to be dispensed through the distal end 16 of the syringe. At its distal end, the syringe is provided with threading 18 in its interior surface, for connection of the distal end of the syringe to a catheter by means of luer-lock or other conventional coupling means.

The interior volume 14 of the syringe is bounded by an interior wall surface 20, as shown. At the proximal end 22 of the syringe is interiorly disposed a plunger 24 according to one embodiment of the present invention. The plunger 24 is of generally converging shape at its distal end, and includes an outer circumferentially continuous edge (side) surface 26 which contacts the inner surface 20 of the syringe. The plunger further includes an array of circumferentially spaced-apart flexible resilient engagement members 30, as hereinafter more fully described.

At the proximal end of the syringe on the exterior surface thereof are provided diametrally opposed flange or lug members 32 and 34, for engaging and locking the syringe in the face structure of a front-load injector, as illustrated in FIG. 2 hereof.

As used herein, the term "diametrally opposed" means that the relevant structural elements are located at opposite sides of a cylindrical or circular element for member of the appertaining apparatus. The diametrally opposed elements for members are thus symmetrically arranged with respect to an associated diameter of the cylindrical or circular part or structure with which they are associated.

In FIG. 2, the corresponding structural elements of the syringe are numbered identically to the drawing of FIG. 1. As shown, the syringe is in exploded relationship to a driving head 40 of frustoconical shape, having a front circular surface 42 with a central set screw 44 therein, and a frustoconical side surface 46. The driving head in this embodiment is integrally formed with a cylindrical color 48 having a side set screw 50 therein. By means of the set screws 44 and 50, the driving head assembly may be secured to the generally rectangular ram tip 52 mounted on reciprocating shaft 54 for forward driving and rearward retraction movement of the ram tip and driving head mounted thereon. The injector apparatus 60 as shown comprises an injector housing 62 with a front face 64 to which is secured a face plate adapter assembly 66. The face plate adapter assembly has a front face 68 with a cylindrical cavity 70 therein and a front slot opening 72 communicating therewith. The face plate adapter assembly as hereinafter described more fully, comprises a lifting ring 74, the purpose of which is to radially outwardly deform the flexible resilient engagement members 30 of the plunger 24 so that the flexible resilient engagement members thereby interact with the face plate adapter assembly 66 to permit engagement (and correspondingly, upon retraction of the ram tip and driving head, disengagement) of the plunger with the driving head.

By the arrangement shown, the front-load angiographic syringe is rearwardly inserted with the flange members 32 and 34 engaging the slot 72 on the face plate adapter assembly 66. After positioning in the slot, the syringe is rotated 90°, to lockingly engage flange members 32 and 34 with an internal groove communicating with the slot and forming a retention flange transverse to the direction of slot 72.

Such engagement of the syringe with the face plate adapter assembly causes the flexible resilient engagement members 30 to be spread by the lifting ring 74 so that the frustoconical driving head then engages the flexible resilient engagement members to thereby couple the syringe through the plunger to the driving head, for subsequent forward translation of the driving head to express contrast media for other fluid from the syringe barrel interior volume through the distal end of the syringe.

Figure 3:
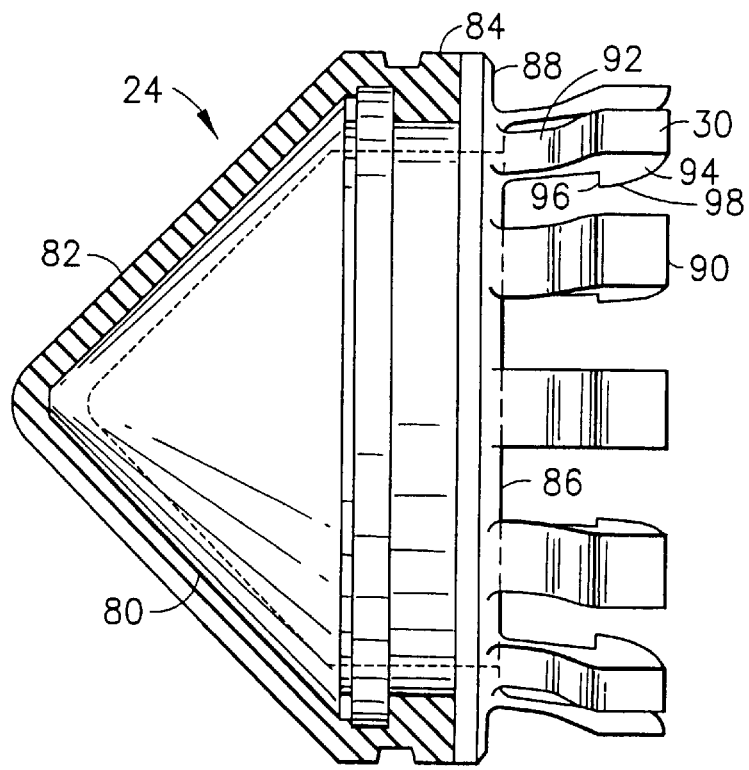
FIG. 3 is a side elevation view of a plunger according to one embodiment of the present invention.

FIG. 3 is a side elevation view of a plunger 24 according to one embodiment of the present invention. The plunger in this embodiment includes a plunger body 80 which may be overlaid by a resilient rubber or hard plastic cover 82 which may be stretch-fitted over the plunger body 80 as shown. Alternatively, the plunger body may be a unitary one piece design without any cover or sheath member. The plunger body with the cover has an outer circumferentially continuous edge surface 84 for engaging an interior surface of the syringe barrel when the plunger is operatively positioned within the syringe barrel.

The proximal face 86 of the plunger body includes a circumferential surface portion 88. An array of circumferentially spaced-apart flexible resilient engagement members 30 is joined to the circumferential surface portion 88 of the proximal face of the plunger body and rearwardly extends therefrom to a rearmost extremity 90. Each of the flexible resilient members has a shank portion 92 rearwardly extending from the circumferential surface portion 88 and terminating in a tail hook portion 94 including a transversely and radially inwardly extending retention surface 96 for matably engagiag with a rear circumferential surface of the driving head of the injector when the driving head is operatively coupled with the plunger. Each tail hook portion at the retention surface 96 is of increased thickness (in the lateral dimension transverse to the length dimension of the flexible resilient engagement member) relative to the shank portion 92 of such member. The tail hook portion is of tapering character from the region of the retention surface 96 in the rearward direction toward the rearmost extremity 90 thereof, and the tail hook portion has in the embodiment shown a convexly shaped inner engagement surface 98 for contacting the frustoconical shaped driving head to circumferentially compressively engage the frustoconical side surface of the driving head with the transversely and radially inwardly extending retention surface 96 engaged with a rear circumferential surface of the driving head when the driving head is engaged with the plunger. The array of flexible resilient engagement members 30 is circumferentially arranged on the circumferential surface portion 88 of the proximal face 86 of the plunger body so that the flexible resilient engagement members are radially inwardly spaced from the outer circumferentially continuous hedge surface of the plunger. The purpose of such radial inset of the engagement members 30 is so that such engagement members do not contact interior surfaces of the syringe barrel during translation of the plunger forwardly or rearwardly through the syringe barrel.

Figure 4:
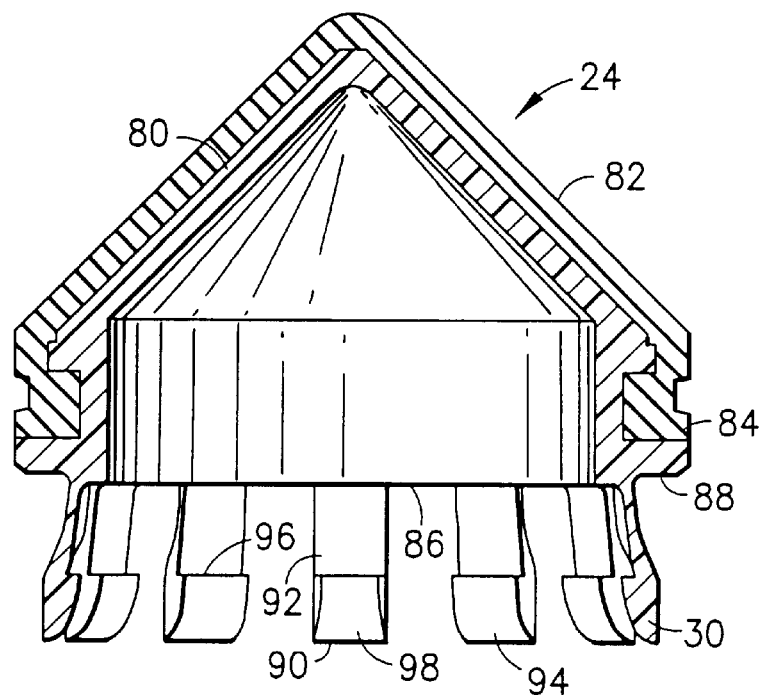
FIG. 4 is a cross-sectional elevation view of a plunger of the type shown in FIG. 3.

FIG. 4 is a cross-sectional elevation view of a plunger of the type shown in FIG. 3 showing the hollowed out interior volume of the plunger body. The plunger alternatively may be of solid-body construction, without such interior cavity.

The plunger body may be formed of any suitable material of construction, such as polyurethane, polyvinylchloride, polymeric rubber or block copolymer composition, or of any suitable material of construction.

Figure 5:
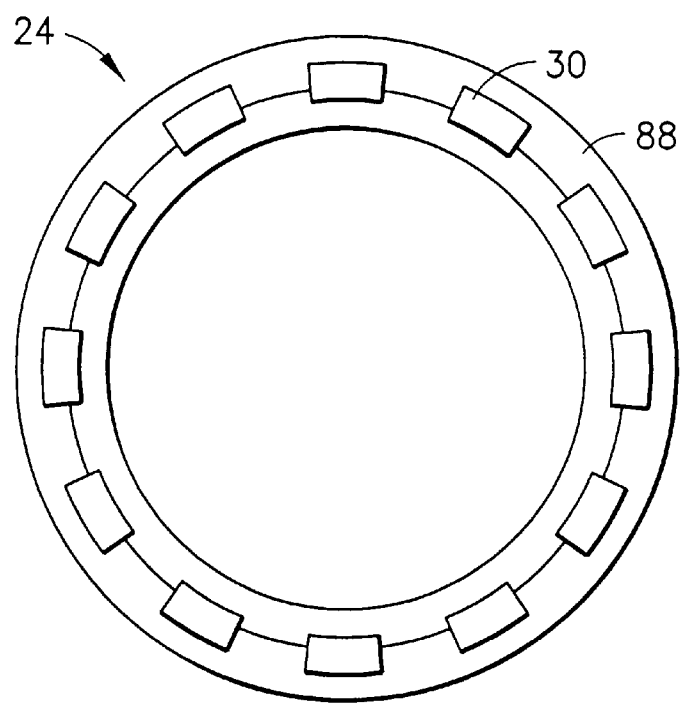
FIG. 5 is a rear plan view of the plunger of FIGS. 3 and 4.

FIG. 5 is a rear plan view of the plunger 24 of FIGS. 3 and 4.

Figure 6:
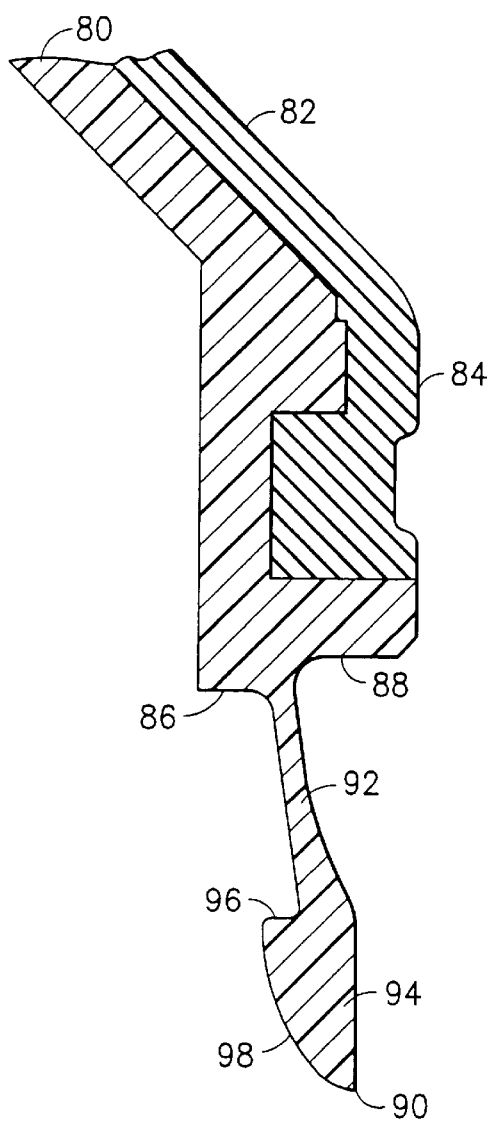
FIG. 6 is a cross-sectional elevation view of a flexible resilient engagement member of the plunger shown in FIGS. 3–5.

FIG. 6 is a cross-sectional elevation view of a single flexible resilient engagement member of the plunger shown in FIGS. 3–5, enlarged to show the structural details thereof.

Figure 7:
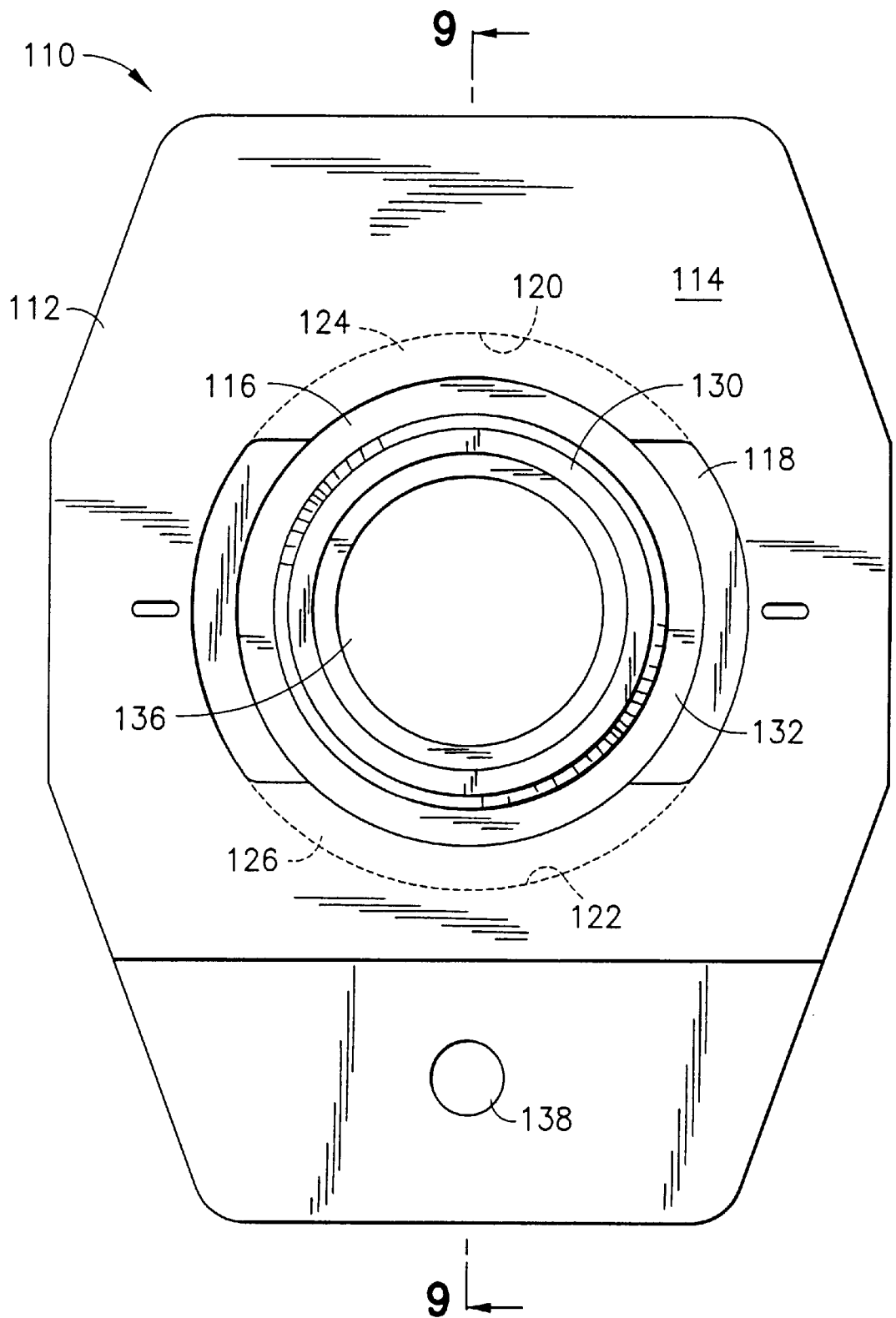
FIG. 7 is a front elevation view of a front-load syringe injector face plate adapter assembly, according to one embodiment of the present invention.

FIG. 7 is a front elevation view of a front-load syringe injector face plate adapter assembly 110, according to one embodiment of the present invention.

As shown, the face plate adapter assembly includes a main body 112 of the shape shown, or any other convenient shape and confirmation for mounting on the face of a front-load injector apparatus.

The front face 114 of the face plate adapter assembly has a cylindrical cavity 116 therein and a front slot opening 118 communicating therewith. The face plate adapter assembly also includes diametrically opposite grooves 120 and 122 communicating with the slot opening 118 and thereby defining diarnetrally opposite retention flange portions 124 and 126 transverse to the slot opening, for engagement with a front-load syringe of the type shown in FIG. 1 having rear flange members 32 and 34 engagable with the slot opening 118 and lockable in position in the face plate adapter assembly by rotation by 90° so that the rear flange members 32 and 34 of the syringe engage the retention flange portions 124 and 126 of the main body of the face plate adapter assembly.

The face plate main body 112 has in the cavity 116 a lifting ring 130 defining an annular volume 132 between the cavity and the lifting ring for engagement with a rear circumferential extremity of a syringe when the syringe is engaged with the face plate adapter assembly. The lifting ring 130 serves to engage with and radially outwardly spread the flexible resilient engagement members 30 of the plunger (see FIG. 2) in the syringe assembly comprising the plunger as illustratively described in connection with FIGS. 1–6.

The main body of the face plate adapter assembly has a central opening 136 in the cavity, allowing passage therethrough of the driving head and ram head mounted on the drive shaft of the injector apparatus. The face plate adapter assembly and the embodiment shown has a hole 138 on a lower portion thereof as shown, to accommodate passage therethrough of a mechanical fastener, such as a screw or bolt for threadably engaging with a registerable opening on the face of the injector apparatus, to insure secure attachment of the face plate adapter assembly to the housing of the injector apparatus. In lieu of a threaded mechanical fastener, the hole 138 may simply accommodate a compression-fit brad or dowel for such securement purpose.

Figure 8:
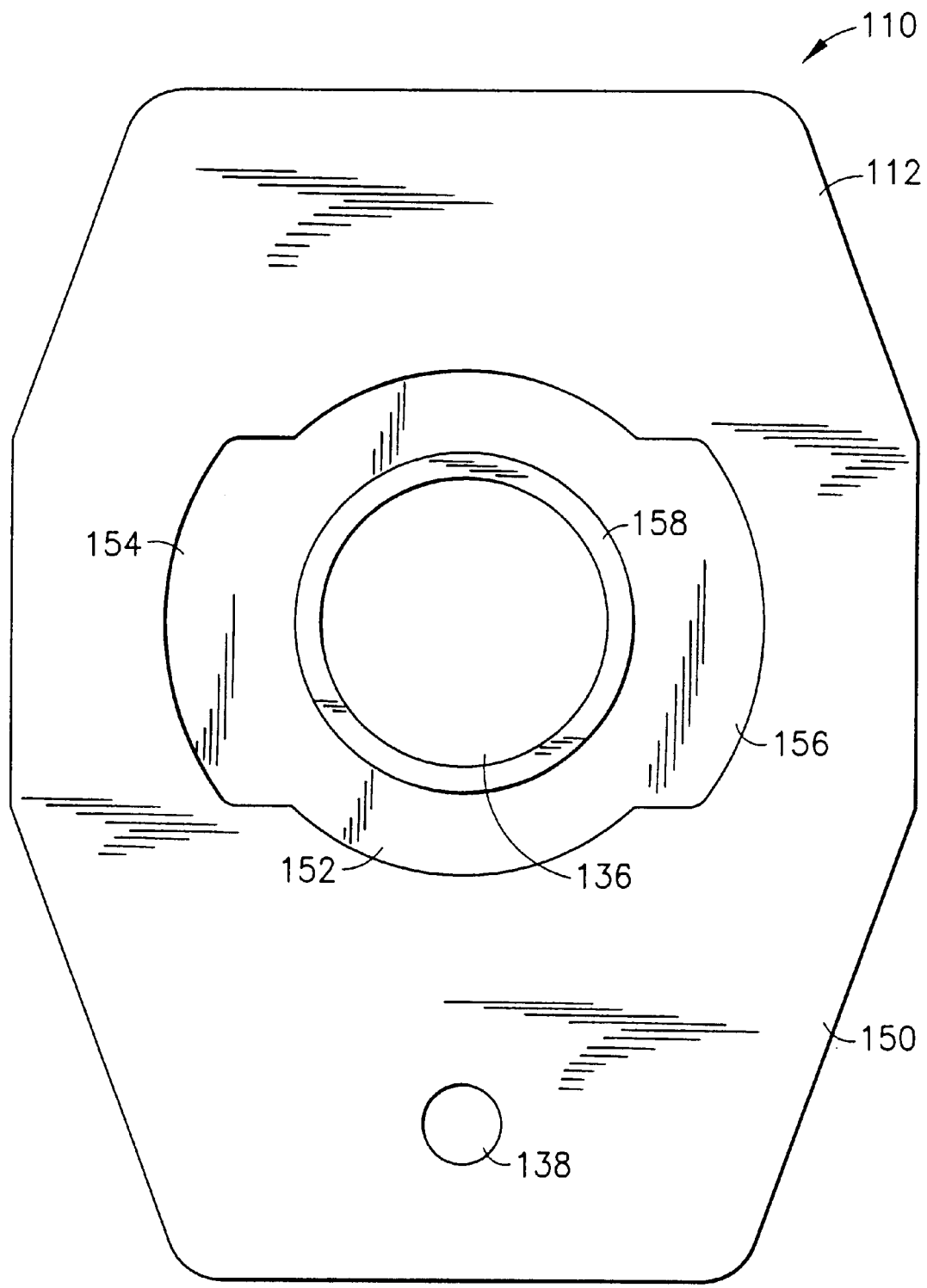
FIG. 8 is a rear elevation view of the face plate adapter assembly of FIG. 7.

FIG. 8 is a rear elevation view of the face plate adapter assembly 110 of FIG. 7.

The face plate adapter assembly main body 112 in this orientation has a rear face 150 of generally flat confirmation, to allow to matable engagement of the face plate adapter assembly with the face of the injector apparatus housing. The rear face has mounted thereon for integrally formed therewith a cylindrical extension 152 with diametrally opposite flange elements 154 and 156 for engaging a matably shaped cavity on a front face of an injector apparatus, and lockable in position by rotation of the main body of the face plate adapter assembly so that the diametrally opposite flange elements 154 and 156 engage retaining flange elements in the face of the injector apparatus. Thus, the face plate adapter assembly is adapted to be mounted on a front-load injector apparatus of the type described in U.S. Pat. No. 5,383,858 issued Jan. 24, 1995 to David M. Reilly, et al.

The cylindrical extension 152 has a cylindrical collar 158 extending outwardly therefrom, for registration with the recipient cavity in the face of the injector apparatus housing. By "matably shaped cavity" on the front face of an injector apparatus is meant a cavity which is shaped so as to be matably engaged with the cylindrical extension and diametrally opposite flange elements on the rear face of the face plate adapter assembly. Thus, the face plate adapter assembly rear face flange elements 154 and 156 are inserted into the slot on the front face of an injector housing and the face plate adapter assembly then is rotated 90° to place the flange elements 154 and 156 into a pair of oppositely positioned slots in the face of the injector housing, so that the flange elements 154 and 156 are retained behind retentive flange portions of the face of the injector housing.

Figure 9:
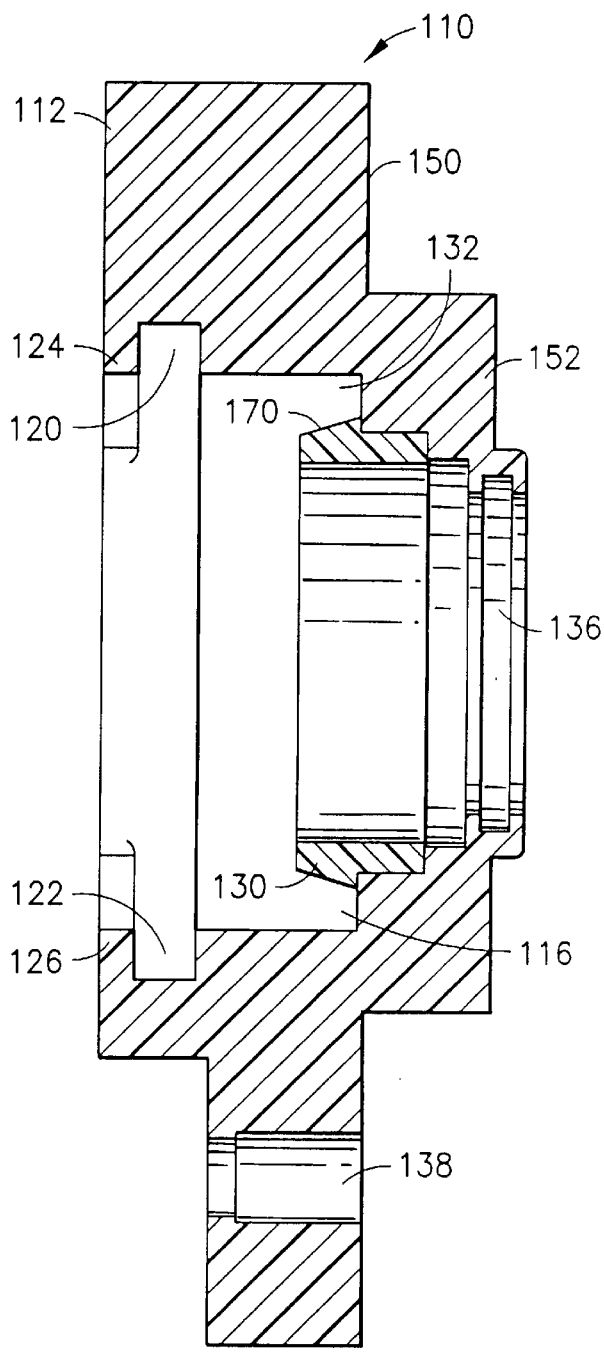
FIG. 9 is a cross-sectional elevation view taken along line A—A of FIG. 7, showing the details of the face plate adapter assembly.

FIG. 9 is a cross-sectional elevation view, taken along line A—A of FIG. 7, showing the details of the face plate adapter assembly.

As shown in FIG. 9, the face plate adapter assembly has a main body 112 with the cross-sectional shape shown, wherein the rear face 150 has the cylindrical extension 152 rearwardly extending therefrom and bounding the central opening 136. The lifting ring 130 is positioned in the cavity 116 and forms the annular volume 132 which receives the proximal extremity of the syringe, with the lifting ring having a beveled outer surface 170 as shown, which serves to engage with the flexible resilient engagement members of the plunger and to radially outwardly deform such engagement members for subsequent engagement with the frustoconical driving head which is forwardly advanced into engagement with the plunger.

Figure 10:
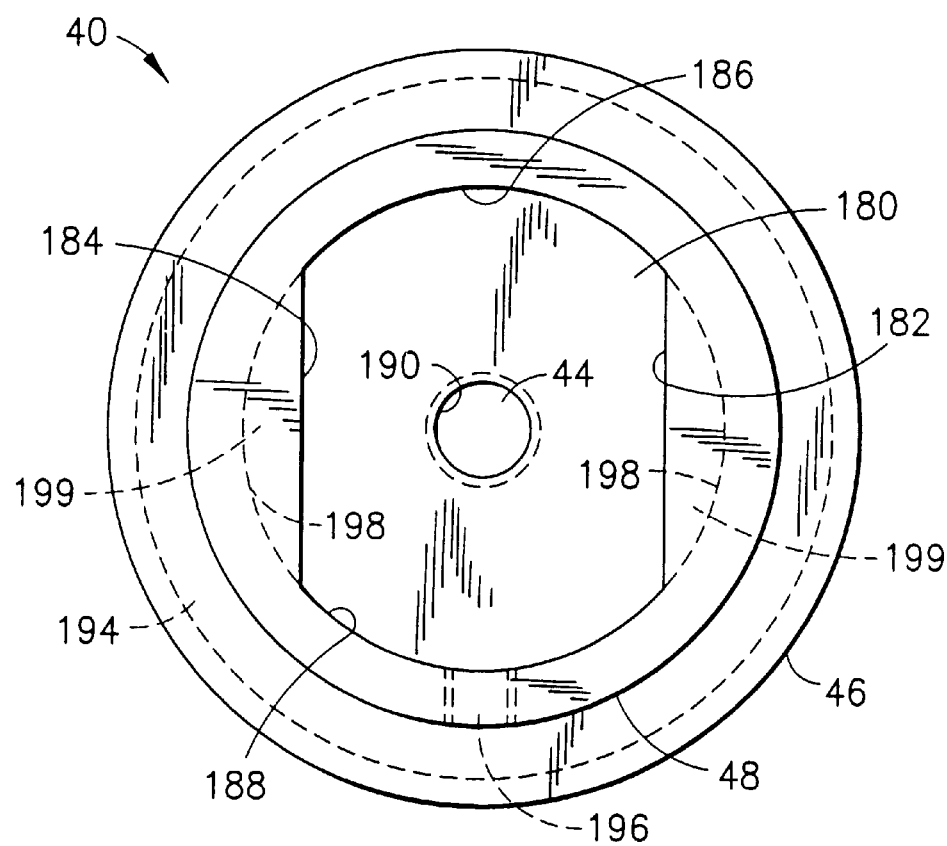
FIG. 10 is a rear elevation view of a driving head assembly utilized with the face plate adapter assembly and plunger of the present invention, in one embodiment thereof.

FIG. 10 is a rear elevation view of a driving head 40 utilized with the face plate adapter assembly and plunger of the present invention, in one embodiment thereof.

The driving head includes a frustoconical side surface 46 (as previously described in connection with FIG. 2), and the frustoconical driving head is joined to a cylindrical collar 48 having an opening 196 therein for a set screw (set screw 50 in FIG. 2). The frustoconical driving head has a central threaded opening 190 therein for receiving a set screw 44 (as also shown in FIG. 2).

The cylindrical collar 48 has a cavity 180 therein bounded by the linear side walls 182 and 184 and the arcuate end walls 186 and 188 to define a cavity for receiving a generally rectangular or complimentarily shaped ram head (see element 52 in FIG. 2) therein, so that the set screw 44 and set screw in threaded opening 196 may be tightenably engaged against the ram head to securely position the frustoconical driving head thereon. For this purpose, the arcuate end walls 186 and 188 may as shown define an interior groove 198 overlaid by wall portion 199 so that the ram head once engaged with the cavity 180 may be rotated relative to the collar 48 of the frustoconical driving head to engage the extremities of the ram tip behind wall segments 199. The rear surface 194 of the frustoconical driving head presents a surface for matable engagement with the engagement surfaces 96 (see for example FIG. 6) of the flexible resilient engagement members of the plunger, while the frustoconical side surface 46 matably engages the inner facing surface of the shank 92 of the flexible resilient engagement member.

Figure 11:
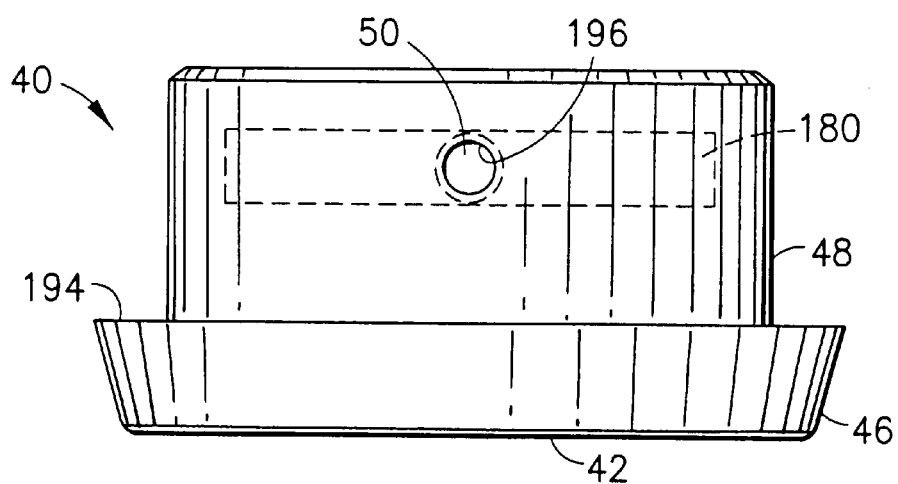
FIG. 11 is a side elevation view of the driving head assembly of FIG. 10.
Figure 12:
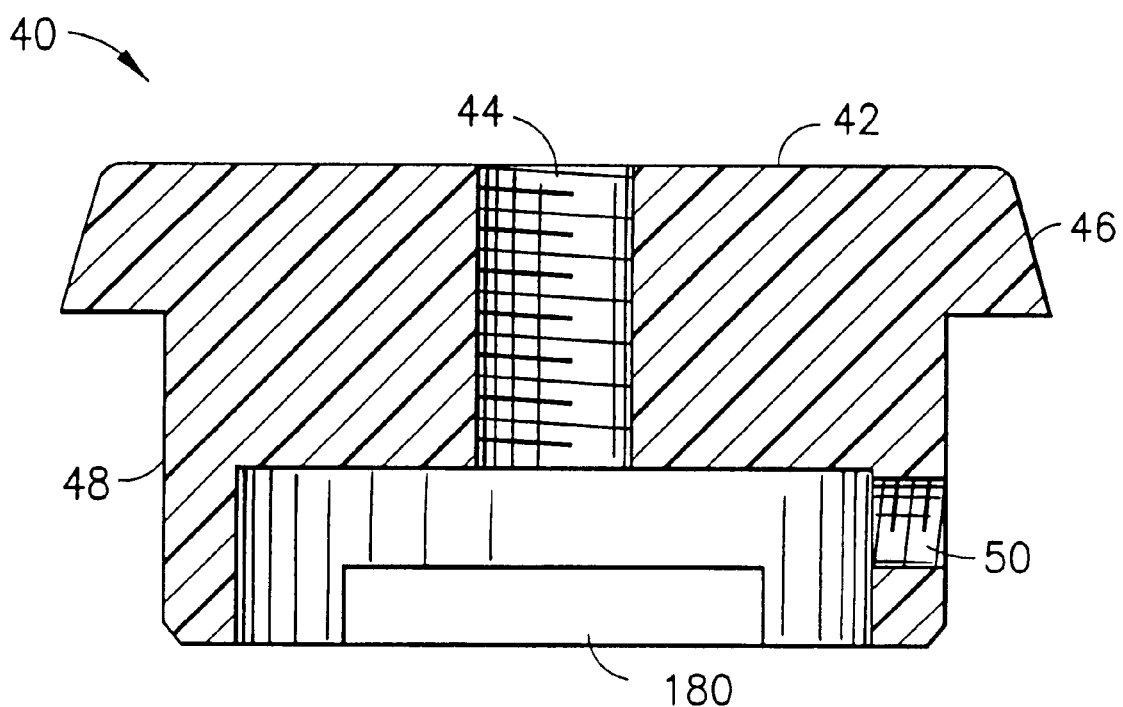
FIG. 12 is a cross-sectional elevation view of the driving head assembly of FIG. 10 and 11.

FIG. 11 is a side elevation view of the driving head assembly of FIG. 10, and FIG. 12 is a cross-sectional elevation view of the driving head assembly showing the set screws 44 and 50 whereby the driving head may be secured to the ram tip of an injector, contemporaneous with securement of the face plate adapter assembly thereto, to permit use of the plunger and angiographic syringe of the present invention therewith.

The embodiment of the invention variously shown and described with reference to FIGS. 1–12 hereof overcomes a significant problem of various prior art plunger and driving head connection/coupling arrangements, namely, their susceptibility to "cocking." Cocking as used in this context refers to the tendency of the plunger to tilt or cock to one side, so as to be off-axis with respect to the longitudinally center line of the syringe. Such mis-alignment can be quite severe in some instances and can result in leakage of contrast media or other contained fluid from the interior volume of the syringe rearwardly to the driving head and injector housing, where it can deleteriously effect the function of the injector apparatus. The plunger arrangement of the present invention of the embodiment previously described minimizes plunger cocking and associated leakage problems.

FIG. 13 is a cross-sectional elevation view of a portion of an angiographic syringe and plunger according to another embodiment of the present invention, shown in coupled relationship to a portion of a face plate adapter assembly of alternative design.

As shown in FIG. 13, the angiographic syringe 210 comprises a syringe barrel 212 whose interior wall surface 214 bounds the interior volume 216 of the syringe.

The interior volume 216 contains a plunger 218 of convergent shape at its distal portion 220. The plunger 218 has a flat proximal surface 222 on which is disposed a plurality of rearwardly extending retention elements 224 and 226, with rearmost portions 228 and 230, respectively, which are shaped for matable engagement with reverse-hooked ends 232 and 234 of projections 236 and 238 of the driving head 240.

The driving head 240 has an outer surface of frustoconical shape as shown, presenting an outer surface 242 which is slideably engagable against the interior wall surface 244 of the receptacle 246 of face plate adapter assembly 250. The face plate adapter assembly is disposed in a budding relationship to the front wall 252 of an injector housing containing the receptacateable shaft 254 which is joined at its distal end to the driving head 240.

By this arrangement, the angiographic syringe 210 at its proximal end is reposed on support element 256, with the retention elements 224 and 226 rearwardly extended. The driving head 240 is drivable in either of the forward or rearward directions, as indicated by bidirectional arrow A. The translation of the driving head by the reciprocateable drive shaft 254 causes the engagement elements 232 and 234 to be deflected in the directions of movement indicated by bidirectional arrows B and C, with the resilient elements being translated radially outwardly by forward movement of the driving head, and radially inwardly by retracting movement of the driving head, as a result of the tapered configuration of the wall surface 244 and the driving head 242 surface.

In operation, the angiographic syringe is positioned as shown, and forward movement of the drive shaft 254 and corresponding advancement of the driving head 240 causes the resilient elements 233 and 234 to move radially outwardly to engage with the matable surfaces 228 and 230, so that the driving head projections bear compressively outwardly against the projection elements of the plunger, to engage the driving head and plunger.

Conversely, when the plunger is retracted by the driving head, and the driving head enters the cavity bounded by conical wall surface 244, the retraction will cause the retention elements 232 and 234 to radially inwardly translate and to disengage from the engagement surfaces of the projections on the plunger.

Thus, it will be seen that the present invention contemplates a front-load angiographic syringe injector system, in which the plunger and driving head are arranged so that at least one of them interacts with the face plate to effect engagement and disengagement of the plunger and driving head relative to one another.

Other arrangements of the plunger, driving head and face plate adapter assembly are contemplated within the broad practice of the invention, wherein at least one of the plunger and driving head elements interacts with the face plate adapter assembly to effect engagement and disengagement of the plunger and driving head elements. For example, the ram may be constructed of a deformable resilient material which is constructed so that rearward pressure of the plunger on the face plate causes localized constriction of a portion of the deformable resilient material of the ram head, causing same to reactively expand against the plunger to effect engagement therewith, and which upon retraction is correspondingly deformed to effect disengagement of the driving head from the plunger.

Thus, while the invention has been described herein with respect to various illustrated features, aspects and embodiments, it will be recognized that the invention is not thus limited, and other variations, modifications and alternative embodiments will readily suggest themselves to those of ordinary skill in the art. Accordingly, the invention is to be broadly construed, consistent with the claims hereafter set forth.

What is claimed is:

1. A face plate adapter assembly for a front-load syringe injector, including a main body having on a rear face thereof a cylindrical extension with diametrically opposite flange elements for engaging a matably shaped cavity on a front face of an injector apparatus, and lockable in position by rotation of the main body portion so that the diametrically opposite flange elements engage retaining flange elements in the face of the injector apparatus, with a front face of the main body portion having a cylindrical cavity therein and a front slot opening communicating therewith with diametrically opposite retention flange portions transverse to the slot opening, for engagement with a front-load syringe having rear flange members engageable with the slot opening and lockable in position in the face plate adapter assembly by rotation so that the rear flange members of the syringe engage the retention flange portions of the main body, the face plate main body having in the cavity a lifting ring defining an annular volume between the cavity and the lifting ring for engagement with a rear circumferential extremity of a syringe when the syringe is engaged with the face plate adapter assembly, the lifting ring serving to engage with and radially outwardly spread the flexible resilient engagement members of a plunger of the syringe, and wherein the plunger comprises:

a plunger body having a generally convergent distal portion, an outer circumferentially continuous edge surface for engaging an interior surface of a syringe barrel when the plunger body is operatively positioned within the syringe barrel, and a proximal face including a circumferential surface portion, with an array of circumferentially spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a driving head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting a frustoconical shaped driving head to compressively engage a frustoconical side surface of the driving head with the transversely radially inwardly extending retention surface matably engaged with a rear circumferential surface of the driving head when the driving head is engaged with the plunger;

the array of circumferentially spaced-apart flexible resilient engagement members being circumferentially arranged on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the syringe barrel.

2. A front-load syringe injector system including a front-load injector apparatus bearing on a front face thereof a face plate adapter assembly, said face plate adapter assembly including a main body having on a rear face thereof a cylindrical extension with diametrically opposite flange elements for engaging a matably shaped cavity on a front face of an injector apparatus, and lockable in position by rotation of the main body portion so that the diametrically opposite flange elements engage retaining flange elements in the face of the injector apparatus, with a front face of the main body portion having a cylindrical cavity therein and a front slot opening communicating therewith with diametrically opposite retention flange portions transverse to the slot opening, for engagement with a front-load syringe having rear flange members engageable with the slot opening and lockable in position in the face plate adapter assembly by rotation so that the rear flange members of the syringe engage the retention flange portions of the main body, the face plate main body having in the cavity a lifting ring defining an annular volume between the cavity and the lifting ring for engagement with a rear circumferential extremity of a syringe when the syringe is engaged with the face plate adapter assembly, the lifting ring serving to engage with and radially outwardly spread the flexible resilient engagement members of a plunger of the syringe;

an angiographic syringe engaged with the face plate adapter assembly, said syringe comprising a plunger including:

a plunger body having a generally convergent distal portion, an outer circumferentially continuous edge surface for engaging an interior surface of a syringe barrel when the plunger body is operatively positioned within the syringe barrel, and a proximal face including a circumferential surface portion, with an array of circumferentially spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a driving head of the injector apparatus when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting a frustoconical shaped driving head to compressively engage a frustoconical side surface of the driving head with the transversely radially inwardly extending retention surface matably engaged with a rear circumferential surface of the driving head when the driving head is engaged with the plunger;

the array of circumferentially spaced-apart flexible resilient engagement members being circumferentially arranged on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the syringe barrel.

3. A front-load syringe injector system comprising:
a. a front-load injector apparatus comprising:
   (i) a driving mechanism;
   (ii) attachment means for disengageably engaging attachment means of a plunger;
b. a face plate adapter assembly operably mounted on the front-load injector apparatus and comprising:
   (i) means for attaching the face plate adapter assembly to the front-load injector apparatus;
   (ii) a generally cylindrical cavity extending through the face plate adapter assembly, arranged such that, during operation, the driving mechanism can move the driving head through the cavity;
c. a plunger having attached thereto attachment means for engaging the attachment means of the driving mechanism, said plunger attachment means comprising a plunger body having a generally convergent distal portion, an outer circumferentially continuous edge surface for engaging an interior surface of a syringe barrel when the plunger body is operatively positioned within the syringe barrel, and a proximal face including a circumferential surface portion, with an array of circumferentially spaced-apart flexible resilient engagement members joined to the circumferential surface portion of the proximal face of the plunger body extending rearwardly therefrom;

the array of circumferentially spaced-apart flexible resilient engagement members being circumferentially arranged on the circumferential surface portion of the proximal face of the plunger so that the flexible resilient engagement members are radially inward spaced from the outer circumferentially continuous edge surface of the plunger, whereby the flexible resilient engagement members do not contact interior surfaces of the syringe barrel during translation of the plunger fowardly or rearwardly through the syringe barrel.

4. A plunger having utility in a power-driven angiographic syringe assembly comprising power driving means including an axially extending reciprocatable drive shaft and a frustoconical shaped driving head attached to said drive shaft, the plunger comprising:

a. a plunger body comprising:
   (i) a distal portion;
   (ii) an outer circumferentially continuous edge surface for engaging an interior surface of a syringe barrel;
   (iii) a proximal face generally opposite the distal portion comprising a circumferential surface portion;
b. an array of circumferentially spaced-apart flexible, resilient engagement members joined to the circumferential surface portion of the proximal face of the plunger body and extending rearwardly therefrom, each of said engagement members comprising:
   (i) a flexible shank portion rearwardly extending from the circumferential surface portion of the proximal face of the plunger;
   (ii) a tail hook portion at a rearward terminus of the shank portion comprising:
      a) a transversely and radially inwardly extending retention surface, having an attachment point and an inner terminus, for matably engaging with a rear circumferential surface of a drive head of an injector when the drive head is operatively coupled with the plunger,
      b) a convexly shaped inner engagement curving rearward generally transverse to and outwardly from the terminus of the retention surface, resulting in a general tapering of the tail hook portion from the retention surface to the rearmost extremity, such that upon contacting a frustoconically shaped driving head, the retention surface can compressively engage a frustoconical side surface of the driving head and the retention surface matably engaged with a rear circumferential surface of the driving head; and
   (iii) the array of engagement members being circumferentially arranged on the circumferential surface portion of the proximal face of the plunger so that the flexible resilient engagement members are radially inwardly spaced from the outer circumferentially continuous edge surface of the plunger, such that the flexible resilient engagement members do not contact interior surfaces of a syringe barrel during translation of the plunger forwardly or rearwardly through the syringe barrel.

5. An angiographic syringe including a plunger having attached thereto attachment means for engaging the attachment means of a driving mechanism of an injector apparatus, said plunger attachment means comprising a plunger body having a generally convergent distal portion, an outer circumferentially continuous edge surface for engaging an interior surface of a syringe barrel, a proximal face including a circumferential surface portion with an array of circumferentially spaced-apart flexible, resilient engagement members joined to the circumferential surface portion of the proximal face of the plunger body and extending rearwardly therefrom; the array of circumferentially spaced-apart flexible resilient engagement members being circumferentially arranged on the circumferential surface portion of the proximal face of the plunger so that the flexible resilient engagement members are radially inward spaced from the outer circumferentially continuous edge surface of the plunger, whereby the flexible resilient engagement members do not contact interior surfaces of the syringe barrel during translation of the plunger forwardly or rearwardly through the syringe barrel.

6. An angiographic front-load syringe injector apparatus including an angiographic syringe according to claim 5.

7. A front-load syringe injector system including the angiographic syringe of claim 5.

8. A front-load syringe injector system comprising:
a. a front-load injector apparatus comprising:
   (i) a driving mechanism;
   (ii) attachment means for disengageably engaging attachment means of a plunger;
b. a face plate adapter assembly operably mounted on the front-load injector apparatus and comprising:
   (i) means for attaching the face plate adapter assembly to the front-load injector apparatus;
   (ii) a generally cylindrical cavity extending through the face plate adapter assembly, arranged such that, during operation, the driving mechanism can move the driving head through the cavity;
c. a plunger body comprising:
   (i) a convergent distal portion;
   (ii) an outer circumferentially continuous edge surface for engaging an interior surface of a syringe barrel;
   (iii) a proximal face generally opposite the distal portion comprising a circumferential surface portion with an array of circumferentially spaced-apart flexible resilient engagement members joined to the proximal face of the plunger body and extending rearwardly therefrom;
   each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a driving head of an injector when the drive head is operatively coupled with the plunger, each tail hook portion at the retention surface being of increased thickness relative to the shank portion of the flexible resilient engagement member, and of tapering character toward a rear most extremity thereof, with a convexly shaped inner engagement surface for contacting a frustoconical shaped driving head to compressively engage a frustoconical side surface of the driving head with the transversely radially inwardly extending retention surface matably engaged with a rear circumferential surface of the driving head when the driving head is engaged with the plunger;
   the array of circumferentially spaced-apart flexible resilient engagement members being circumferentially arranged on the circumferential surface portion of the proximal face of the plunger so that the flexible resilient engagement members are radially inwardly spaced from the circumferentially continuous edge surface of the plunger, whereby the flexible resilient engagement members do not contact interior surfaces of the syringe barrel during translation of the plunger forwardly or rearwardly through the syringe barrel.

9. A face plate adapter assembly for a front-load syringe injector comprising:
a. a face plate main body comprising:
   (i) a rear face having a cylindrical extension attached thereto;
   (ii) diametrically opposite flange elements attached to the cylindrical extension;
   (iii) a front face opposite the rear face having a cylindrical cavity therein;
   (iv) diametrically opposite retention flange portions extending from a perimeter of the cylindrical cavity towards the center of the cylindrical cavity and leaving slot openings transverse to the flange portions;
   (v) a lifting ring concentrically positioned within the cylindrical cavity of the front face serving to engage with and spread radially outwardly flexible resilient engagement members of a plunger of the syringe;
   (vi) an annular volume exterior to the lifting ring for engagement with a rear circumferential extremity of the syringe;
b. a plunger body engageable with the driving head and the main body and comprising:
   (i) a distal portion,
   (ii) an outer circumferentially continuous edge surface for engaging an interior surface of a syringe barrel;
   (iii) a proximal face generally opposite the convergent distal portion and having a circumferential surface portion;
c. an array of circumferentially spaced-apart flexible, resilient engagement members joined to the circumferential surface portion of the proximal face and extending rearwardly therefrom, each of said flexible resilient engagement members comprising:
   (i) a flexible shank portion rearwardly extending from the circumferential surface portion of the proximal face of the plunger;
   (ii) a tail hook portion attached at a rearward terminus of the shank portion and comprising a transversely and radially inwardly extending retention surface for matably engaging with a rear circumferential surface of a driving head of an injector when the drive head is operatively coupled with the plunger, the retention surface being of increased thickness relative to the shank portion of the flexible resilient engagement member, and of tapering character toward a rearmost extremity thereof, with a convexly shaped inner engagement surface for contacting a frustoconically shaped driving head to compressively engage a frustoconical side surface of the driving head;
the flexible resilient engagement members being circumferentially arranged such that the flexible resilient engagement members converge towards a center of the outer circumferentially continuous edge surface of the plunger, such that the flexible resilient engagement members do not contact interior surfaces of the syringe barrel during translation of the plunger forwardly or rearwardly through the syringe barrel.

10. A front-load syringe injector system comprising:
a. a front-load injector apparatus comprising a face plate adapter assembly comprising:
   (i) a main body;
   (ii) a cylindrical extension on a rear face of the main body;
   (iii) diametrically opposite flange elements extending outwardly from the cylindrical extension for engaging a matably shaped cavity on a front face of an injector apparatus and lockable in position by rotation of the main body portion so that the diametrically opposite flange elements engage retaining flange elements in the face of the injector apparatus,
   (iv) a front face of the main body portion having a cylindrical cavity therein;
   (v) diametrically opposite retention flange portions extending radially inwardly from a perimeter of the cylindrical cavity;
   (vi) slot openings transverse to the flange portion for engagement with a front-load syringe having rear flange members engageable with the slot openings and lockable in position in the face plate adapter assembly by rotation so that the rear flange members of the syringe engage the retention flange portions of the main body, (vii) a lifting ring concentrically positioned within the cylindrical cavity of the front face serving to engage with and spread radially outwardly flexible resilient members of a plunger of the syringe;

(viii) an annular volume defined by an outer surface of the lifting ring and an inner surface of the cylindrical cavity of the front face for engagement with a rear circumferential extremity of a syringe when the syringe is engaged with the face plate adapter assembly;

b. an angiographic syringe engaged with the face plate adapter assembly, said syringe comprising a plunger comprising:

(i) a distal portion, (ii) an outer circumferentially continuous edge surface for engaging an interior surface of a syringe barrel;

(iii) a proximal face generally opposite the convergent distal portion and having a circumferential surface portion;

(iv) an array of circumferentially spaced-apart flexible, resilient engagement members joined to the circumferential surface portion of the proximal face and extending rearwardly therefrom, each of said flexible resilient engagement members comprising:

a) a flexible shank portion rearwardly extending from the circumferential surface portion of the proximal face of the plunger;

b) a tail hook portion attached at a rearward terminus of the shank portion and comprising a transversely and radially inwardly extending retention surface for matably engaging with a rear circumferential surface of a driving head of an injector when the drive head is operatively coupled with the plunger, the retention surface being of increased thickness relative to the shank portion of the flexible resilient engagement member, and of tapering character toward a rearmost extremity thereof, with a convexly shaped inner engagement surface for contacting a frustoconically shaped driving head to compressively engage a frustoconical side surface of the driving head;

the flexible resilient engagement members being circumferentially arranged such that the flexible resilient engagement members are converge towards a center of the outer circumferentially continuous edge surface of the plunger, such that the flexible resilient engagement members do not contact interior surfaces of the syringe barrel during translation of the plunger forwardly or rearwardly through the syringe barrel.

11. An angiographic syringe including a plunger having utility in a power-driven angiographic syringe assembly comprising power driving means including an axially extending reciprocatable drive shaft and a frustoconical shaped driving head attached to said drive shaft, the plunger comprising:

a. a plunger body comprising:

(i) a distal portion;

(ii) an outer circumferentially continuous edge surface for engaging an interior surface of a syringe barrel;

(iii) a proximal face generally opposite the distal portion comprising a circumferential surface portion;

b. an array of circumferentially spaced-apart flexible, resilient engagement members joined to the circumferential surface portion of the proximal face of the plunger body and extending rearwardly therefrom, each of said engagement members comprising:

(i) a flexible shank portion rearwardly extending from the circumferential surface portion of the proximal face of the plunger;

(ii) a tail hook portion at a rearward terminus of the shank portion comprising:

a) a transversely and radially inwardly extending retention surface, having an attachment point and an inner terminus, for matably engaging with a rear circumferential surface of a drive head of an injector when the drive head is operatively coupled with the plunger, b) a convexly shaped inner engagement curving rearward generally transverse to and outwardly from the terminus of the retention surface, resulting in a general tapering of the tail hook portion from the retention surface to the rearmost extremity, such that upon contacting a frustoconically shaped driving head, the retention surface can compressively engage a frustoconical side surface of the driving head and the retention surface matably engaged with a rear circumferential surface of the driving head; and the array of engagement members being circumferentially arranged on the circumferential surface portion of the proximal face of the plunger so that the flexible resilient engagement members are radially inwardly spaced from the outer circumferentially continuous edge surface of the plunger, such that the flexible resilient engagement members do not contact interior surfaces of a syringe barrel during translation of the plunger forwardly or rearwardly through the syringe barrel.

12. A front-load syringe injector system including the angiographic syringe of claim 11.

13. An angiographic syringe including a plunger having attached thereto attachment means comprising a plunger body having a generally convergent distal portion, an outer circumferentially continuous edge surface for engaging an interior surface of a syringe barrel when the plunger body is operatively positioned within the syringe barrel, and a proximal face including a circumferential surface portion, with an array of circumferentially spaced-apart flexible resilient engagement members joined to the circumferential surface portion of the proximal face of the plunger body extending rearwardly therefrom, the array of circumferentially spaced-apart flexible resilient engagement members being circumferentially arranged on the circumferential surface portion of the proximal face of the plunger so that the flexible resilient engagement members are radially inward spaced from the outer circumferentially continuous edge surface of the plunder, whereby the flexible resilient engagement members do not contact interior surfaces of the syringe barrel during translation of the plunger forwardly or rearwardly through the syringe barrel.

14. A front-load syringe injector system including the angiographic syringe of claim 13.

15. A plunger for a front-load syringe injector system comprising:

a. a circumferential surface for engaging the inner surface of a syringe barrel; and b. a proximal face having attached thereto two or more flexible shank members extending rearwardly therefrom, said flexible shank members comprising a tail hook portion at a rearward terminus of the shank portion, said tailhook portion comprising a retention surface, and said flexible shank members being configured so that they do not touch the syringe barrel upon entry thereinto.

16. The plunger of claim 15 further comprising a conical front face.

17. The plunger of claim 15 wherein the flexible shank members are radially positioned around a circumference of the proximal face of the plunger.

18. The plunger of claim 15 comprising 3 or more flexible shank members radially positioned around a circumference of the proximal face of the plunger.

19. The plunger of claim 15 comprising 4 or more flexible shank members radially positioned around a circumference of the proximal face of the plunger.

20. The plunger of claim 15 wherein the hook portions of the tail hook members face inwardly.

21. The plunger of claim 15 wherein the tail hook portions further comprise an engagement surface curving rearward generally transverse to and away from a terminus of the retention surface, to provide in a general tapering of the tail hook portion from the retention surface to the rearmost extremity.

22. The plunger of claim 21 wherein the engagement surface is convexly shaped.

23. The plunger of claim 21 configured such that upon contacting a frustoconically shaped driving head, the retention surface compressively engages a frustoconical side surface of the driving head and the retention surface matably engages with a rear circumferential surface of the driving head.

24. The plunger of claim 15 wherein the plunger is engageable while the plunger is positioned within the syringe barrel such that the hook members no not extend outside the syringe barrel.

25. An angiographic syringe comprising:
   a. a syringe barrel, and
   b. a plunger comprising;
      (i) a circumferential surface for engaging the inner surface of a syringe barrel; and
      (ii) a proximal face having attached thereto two or more flexible shank members extending rearwardly therefrom, said flexible shank members comprising a tail hook portion at a rearward terminus of the shank portion, said tailhook portion comprising a retention surface, and said flexible shank members being configured such that such members do not touch the syringe barrel upon entry thereinto.

26. The angiographic syringe of claim 25 wherein the plunger further comprises a conical front face.

27. The angiographic syringe of claim 25 wherein the flexible shank members are radially positioned around the circumference of the proximal face of the plunger.

28. The angiographic syringe of claim 25 wherein the plunger further comprises 3 or more flexible shank members radially positioned around the circumference of the proximal face of the plunger.

29. The angiographic syringe of claim 25 wherein the plunger further comprises 4 or more flexible shank members radially positioned around the circumference of the proximal face of the plunger.

30. The angiographic syringe of claim 25 wherein the hook portions of the plunger face inwardly.

31. The angiographic syringe of claim 25 wherein the tail hook portions of the plunger further comprise an engagement surface curving rearward generally transverse to and away from a terminus of the retention surface, to provide a general tapering of the tail hook portion from the retention surface to the rearmost extremity.

32. The angiographic syringe of claim 31 wherein the engagement surface is convexly shaped.

33. The angiographic syringe of claim 31 wherein the plunger is configured such that, upon contacting a frustoconically shaped driving head, the retention surface compressively engages a frustoconical side surface of the driving head and the retention surface matably engages with a rear circumferential surface of the driving head.

34. The angiographic syringe of claim 25 wherein the plunger is configured such that the plunger is engageable while the plunger is positioned within the syringe barrel such that the hook members no not extend outside the syringe barrel.

35. An angiographic injector system comprising:
   a. a driving mechanism including a driving head;
   b. a face plate adapter assembly operably mounted on the front-load injector apparatus and comprising:
      (i) means for attaching the face plate adapter assembly to the front-load injector apparatus;
      (ii) a cavity extending through the face plate adapter assembly, arranged such that, during operation, the driving mechanism can move the driving head through the cavity; and
      (iii) means for attaching a syringe barrel to the face plate adapter assembly;
   c. a plunger comprising:
      (i) a circumferential surface for engaging the inner surface of a syringe barrel; and
      (ii) a proximal face having attached thereto two or more flexible shank members extending rearwardly therefrom, said flexible shank members comprising a tail hook portion at a rearward terminus of the shank portion, said tailhook portion comprising a retention surface, and said flexible shank members being configured such that such members do not touch the syringe barrel upon entry thereinto.

36. The angiographic injector system of claim 35 wherein the plunger further comprises a conical front face.

37. The angiographic injector system of claim 35 wherein the flexible shank members are radially positioned around the circumference of the proximal face of the plunger.

38. The angiographic injector system of claim 35 wherein the plunger further comprises 3 or more flexible shank members radially positioned around the circumference of the proximal face of the plunger.

39. The angiographic injector system of claim 35 wherein the plunger further comprises 4 or more flexible shank members radially positioned around the circumference of the proximal face of the plunger.

40. The angiographic injector system of claim 35 wherein the hook portions of the plunger face inwardly.

41. The angiographic injector system of claim 35 wherein the tail hook portions of the plunger further comprise an engagement surface curving rearward generally transverse to and outwardly from a terminus of the retention surface, to provide 0a general tapering of the tail hook portion from the retention surface to the rearmost extremity.

42. The angiographic injector system of claim 41 wherein the engagement surface is convexly shaped.

43. The angiographic injector system of claim 41 wherein the plunger is configured such that upon contacting a frustoconically shaped driving head, the retention surface compressively engages a frustoconical side surface of the driving head and the retention surface matably engages with a rear circumferential surface of the driving head.

44. The angiographic injector system of claim 41 wherein the plunger is configured such that the plunger is engageable while the plunger is positioned within the syringe barrel such that the hook members no not extend outside the syringe barrel.

45. The angiographic injector system of claim 41 wherein the face plate further comprises a lifting ring positioned such that as the plunger is fully retracted, the lifting ring engages the convexly shaped inner engagement surface and forces the tailhook portions to disengage the driving head.

46. The angiographic injector system of claim 45 wherein the lifting ring further comprises a conical side face for engagement with the convexly shaped inner engagement surface of the tail hook portions.

47. The angiographic injector system of claim 41 wherein the driving head comprises:
   a. means for forcing the tail hook portions outward upon initial engagement with the inner engagement surface; and
   b. means to permit the tail hook portions to flex inwardly as the driving head is moved from the position of initial engagement to a position of locking engagement with the driving head.

48. The angiographic injector system of claim 41 wherein:
   a. the driving head comprises:
      (i) means for forcing the tail hook portions outward upon initial engagement with the inner engagement surface; and
      (ii) means to permit the tail hook portions to flex inwardly as the driving head is moved from the position of initial engagement to a position of locking engagement with the driving head; and
   b. the face plate further comprises a lifting ring positioned such that as the plunger is fully retracted, the lifting ring engages the engagement surface and thereby forcing the tailhook portions to disengage the driving head.

\* \* \* \* \*

UNITED STATES PATENT AND TRADEMARK OFFICE
CERTIFICATE OF CORRECTION

PATENT NO. : 5,947,929
DATED : September 7, 1999
INVENTOR(S) : Michael W. Trull

It is certified that error appears in the above-identified patent and that said Letters Patent is hereby corrected as shown below:

Column 18, Line 50, change "plunder" to --plunger--

Signed and Sealed this

Twenty-ninth Day of February, 2000

Attest:

Q. TODD DICKINSON

Attesting Officer

Commissioner of Patents and Trademarks